US010777200B2

(12) United States Patent
Will et al.

(10) Patent No.: US 10,777,200 B2
(45) Date of Patent: Sep. 15, 2020

(54) ARTIFICIAL INTELLIGENCE FOR MITIGATING EFFECTS OF LONG-TERM COGNITIVE CONDITIONS ON PATIENT INTERACTIONS

(71) Applicant: International Business Machines Corporation, Armonk, NY (US)

(72) Inventors: Scott A. Will, Louisburg, NC (US); Quang T. N. Duong, Austin, TX (US); David L. Schmidt, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 126 days.

(21) Appl. No.: 16/047,602

(22) Filed: Jul. 27, 2018

(65) Prior Publication Data

US 2020/0035240 A1  Jan. 30, 2020

(51) Int. Cl.
*G10L 15/24* (2013.01)
*G06F 3/01* (2006.01)
*G16H 20/70* (2018.01)
*G06N 20/00* (2019.01)
*G06F 16/36* (2019.01)

(52) U.S. Cl.
CPC .............. *G10L 15/24* (2013.01); *G06F 3/011* (2013.01); *G06F 16/367* (2019.01); *G06N 20/00* (2019.01); *G16H 20/70* (2018.01)

(58) Field of Classification Search
CPC .......................... A61B 5/04012; A61B 5/4836
USPC ............................................................ 704/271
See application file for complete search history.

(56) References Cited

U.S. PATENT DOCUMENTS

| | | | |
|---|---|---|---|
| 7,499,894 B2* | 3/2009 | Marom | A61N 1/36021 706/23 |
| 9,339,227 B2* | 5/2016 | D'arcy | A61B 5/0484 |
| 2014/0364230 A1* | 12/2014 | Borghese | A63F 13/33 463/34 |

(Continued)

OTHER PUBLICATIONS

"Artificial intelligence system provides therapy for cerebral stroke sufferers", Medical Xpress, Apr. 21, 2015, 4 pages.

(Continued)

*Primary Examiner* — Bharatkumar S Shah
(74) *Attorney, Agent, or Firm* — Stephen J. Walder, Jr.; Feb R. Cabrasawan

(57) ABSTRACT

Mechanisms are provided for mitigating the effects of long term cognitive conditions on patient interactions by providing artificial intelligence mechanisms to assist with such interactions. The mechanisms perform a machine learning operation to learn, for a particular patient, associations between patient indicators and concepts that the patient is attempting to communicate or concepts representing actions that the patient would like to perform within a patient environment. The mechanisms receive, from a monitoring device in a patient environment, a patient input representing an attempt by the patient to communicate a concept or interact with the patient environment. The mechanisms perform a cognitive translation of one or more patient indicators in the patient input to one or more corresponding concepts based on results of the machine learning operation. The mechanisms then generate a translation output specifying the one or more corresponding concepts.

20 Claims, 4 Drawing Sheets

(56) References Cited

U.S. PATENT DOCUMENTS

2015/0213225 A1* 7/2015 Amarasingham ....... G06F 19/00
                                                     705/2
2016/0180042 A1* 6/2016 Menon .................. A61B 6/501
                                                     705/2
2019/0224441 A1* 7/2019 Poltorak .............. A61B 5/0006

OTHER PUBLICATIONS

"What are the Different Types of Aphasia?", National Aphasia Association, accessed online Jul. 25, 2018, 8 pages.
"What is Wernicke's Aphasia?", The Aphasia Center, Jan. 28, 2012, 2 pages.
Blom-Smink, Marieke et al., "Prediction of everyday verbal communicative ability of aphasic stroke patients after inpatient rehabilitation", Aphasiology, vol. 31, No. 12, pp. 1379-1391, Published online Mar. 1, 2017, 15 pages.
Dietsche, Erin, "MedyMatch, Samsung NeuroLogica bring AI to stroke care", MedCity News, Mar. 30, 2017, 5 pages.
Maddox, Teena, "New study shows how AI can improve recovery in stroke patients", TechRepublic, Apr. 7, 2017, 9 pages.
Masson, Veronique et al., "Application of artificial intelligence to aphasia treatment", IEA/AIE '90 Proceedings of the 3rd international conference on Industrial and engineering applications of artificial intelligence and expert systems—vol. 2, Jul. 16-19, 1990, pp. 907-913.

\* cited by examiner

ARTIFICIAL INTELLIGENCE FOR MITIGATING EFFECTS OF LONG-TERM COGNITIVE CONDITIONS ON PATIENT INTERACTIONS

BACKGROUND

The present application relates generally to an improved data processing apparatus and method and more specifically to mechanisms for mitigating the effects of long term cognitive conditions on patient interactions by providing artificial intelligence mechanisms to assist with such interactions.

Many medical conditions may have long-term effects on the way that a patient is able to communicate and interact with other persons and their environment. In particular, various types of brain injuries make it difficult for patients to communicate with other persons and may make it difficult for the patient to interact with their environment due to the cognitive impact on the patient. Adding to the complexity of this problem is the fact that each patient is an individual and different from each other patient with regard to the way in which that patient communicates concepts and interacts with his/her environment. Thus, when afflicted with a brain injury, their communication and interaction abilities, which may have been unique to them originally, may be even more uniquely associated with that particular patient due to the particular ways in which the patient's cognitive capabilities are affected by the affliction.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to specifically configure the at least one processor to implement a cognitive patient translation system. The method comprises performing a machine learning operation, by the cognitive patient translation system, to learn, for a particular patient, associations between patient indicators and concepts that the patient is attempting to communicate or concepts representing actions that the patient would like to perform within a patient environment. The method further comprises receiving, from a monitoring device in a patient environment, a patient input representing an attempt by the patient to communicate a concept or interact with the patient environment. Moreover, the method comprises performing, by the cognitive patient translation system, a cognitive translation of one or more patient indicators in the patient input to one or more corresponding concepts based on results of the machine learning operation. Furthermore, the method comprises generating, by the cognitive patient translation system, a translation output specifying the one or more corresponding concepts.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
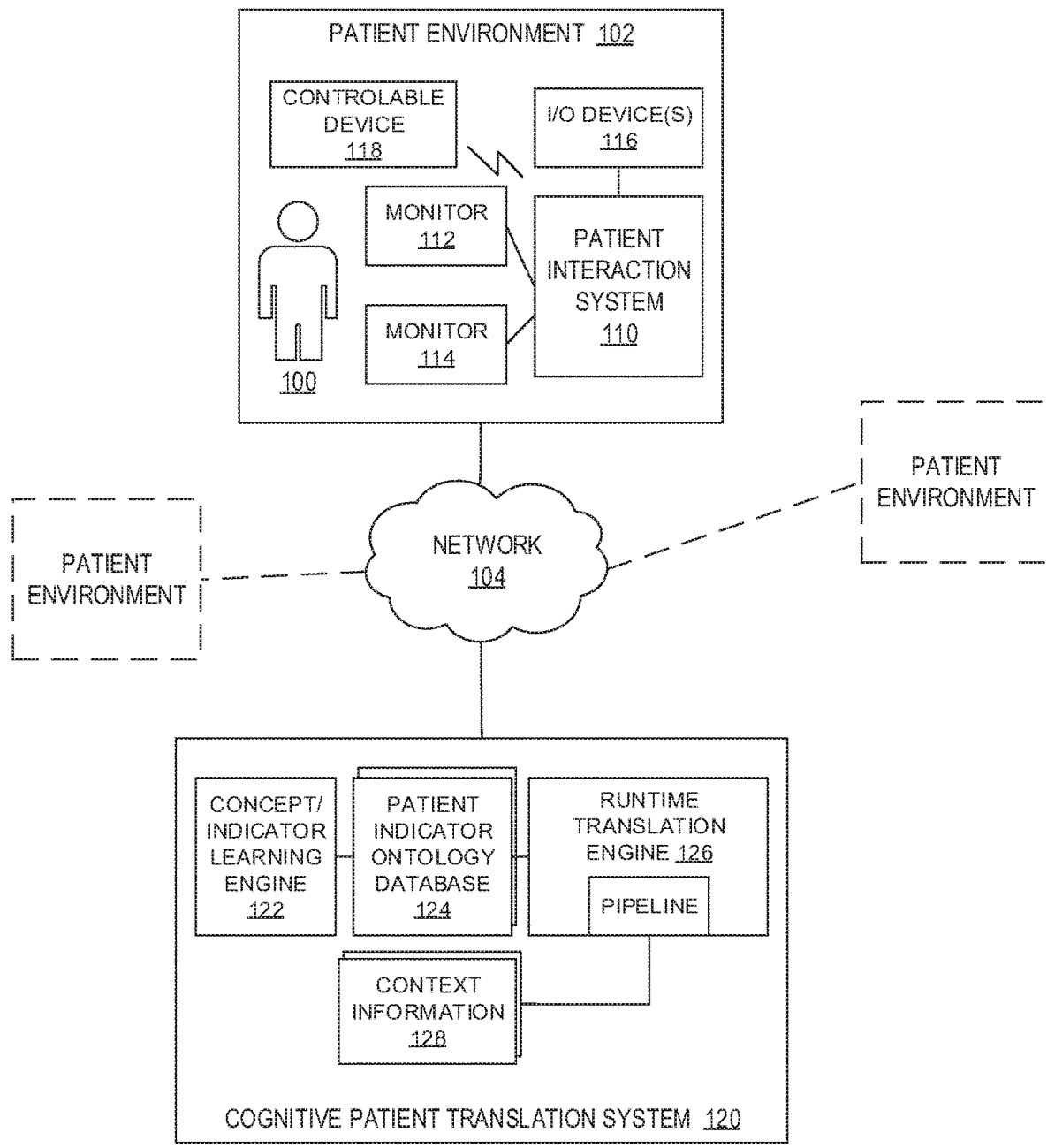
FIG. 1 is an example block diagram illustrating an example of the primary operational elements of one illustrative embodiment and their interactions for facilitating learning and translation of patient indicators.

The illustrative embodiments provide artificial intelligence mechanisms for assisting patients, afflicted with medical conditions that affect their cognitive capabilities, in communicating with other persons and with interacting with their environment. The artificial intelligence mechanisms of the illustrative embodiments learn the specific ways in which the particular patient communicates specific concepts and interacts with their environment (these are referred to herein collectively as the patient's interaction methodologies). The artificial intelligence mechanisms of the illustrative embodiments use the learned patient interaction methodologies to perform assistive actions to assist the patient in their communications and/or interactions with others and their environment. Such assistive actions may comprise, for example, translating audible, motion or gesture, or written communications of the patient that may not be readily understandable by others, into the concepts that the patient is meaning to convey. Such assistive actions may also comprise issuing or transmitting commands to devices within the patient's current environment to affect a change in the environment, e.g., turning on/off electronic devices, lights, etc., or performing any action that a smart home type system may perform, for example. It should be appreciated that the patient's environment may be any environment in which the patient is physically present and may include any personal locations (e.g., home location, work location, or the like), as well as locations that may be more medical and/or convalescent in nature, e.g., skilled nursing facilities, assisted living facilities, etc.

The patient interaction methodologies comprise patient indicators, which may be audible, motion or gesture based indicators, written words/shapes/contours indicators, or the like, that the patient uses to indicate a particular concept. The concept itself may be any person, place, thing, action, feeling, or the like that the patient may wish to communicate. In some illustrative embodiments, the particular recognizable concepts with which the illustrative embodiments operate may be limited to a finite number of key concepts that are used by the patient in their daily life so as to facilitate interactions with the patient to respond to the patient's daily needs.

As mentioned above, many different types of medical conditions may affect the way in which a patient is able to communicate and/or interact with persons and their environment. Such medical conditions tend to be due to brain injury or damage and/or conditions that affect the nervous system and/or muscular system of the human body which in turn affect communication abilities of the patient. For example, cerebral infarctions, or strokes, occur when there is a lesion on the brain, i.e. brain cells die due to loss of oxygen, which may change the cognitive capability, motor function, and the like, of the patient. Such brain injuries may cause changes in the way the human brain operates that affect the way in which the patient can communicate and interact. Moreover, nervous system and/or muscular system conditions may make it physically difficult for some patients to communicate or interact in the manner that they previously did prior to the medical condition, e.g., a patient may not be able to move their mouth to form the specific words for a concept but may be able to make sounds or certain alternative gestures.

One specific type of traumatic brain injury (TBI) that will be used as an example for illustrating the mechanisms of the illustrative embodiments is Wernicke's aphasia. It should be appreciated that while Wernicke's aphasia will be used as an example, the illustrative embodiments are not limited to applicability to only patients afflicted with Wernicke's aphasia and may instead by implemented with or applied to any medical condition that may cause a cognitive and/or communication impairment resulting in a difficulty in communication and/or interaction with the patient's environment. The mechanisms of the illustrative embodiments are especially well suited to situations in which the cognitive and/or communication impairment is a long term condition rather than short term injuries that may heal quickly with a restoring of the cognitive/communication capabilities of the patient.

Wernicke's aphasia is a form of aphasia (i.e. a loss of ability to understand or express speech, caused by brain damage) in which the ability to grasp the meaning of written and spoken words and sentences is impaired, while the ease of producing connected speech is not very affected. Patients with Wernicke's aphasia demonstrate fluent speech, which is characterized by typical speech rate, intact syntactic abilities, and effortless speech output. Writing often reflects speech in that it tends to lack content or meaning. In most cases, motor deficits (e.g., hemiparesis) do not occur in individuals with Wernicke's aphasia. Therefore, they may produce a large amount of speech without much meaning. Individuals with Wernicke's aphasia are typically unaware of their errors in speech and do not realize their speech may lack meaning. They typically remain unaware of even their most profound language deficits.

Like many acquired language disorders, Wernicke's aphasia can be experienced in many different ways and to many different degrees. Patients diagnosed with Wernicke's aphasia can show severe language comprehension deficits, however this is dependent on the severity and extent of the lesion. Severity levels may range from being unable to understand even the simplest spoken and/or written information, to missing minor details of a conversation. Many diagnosed with Wernicke's aphasia have difficulty with repetition in words and sentences, and or working memory.

With regard to patients afflicted with Wernicke's aphasia, the illustrative embodiments provide a mechanism to assist these patients, as well as assist family members, caregivers, and any other persons with which the patient communicates or interacts, in understanding what the patient is attempting to communicate. Moreover, given that the impact of a stroke or other brain injury that results in Wernicke's aphasia is different for every patient, the illustrative embodiments provide artificial intelligence mechanisms that are able to learn how to mitigate the effects of Wernicke's aphasia on an individual basis for the particular patient and the particular way in which the stroke or other medical condition has affected the patient's ability to communicate and interact. That is, the artificial intelligence tool of the illustrative embodiments learns the particular way in which the particular patient communicates concepts and customizes the translation of patient indicators (e.g., audible utterances, motions or gestures, written terms, shapes, contours, or the like) to the particular learned associations of patient indicators with concepts for that particular patient.

In general, in accordance with some illustrative embodiments, an artificial intelligence tool is provided and implemented, at least partially, within a patient's environment. The artificial intelligence tool may be implemented as one or more computing devices specifically configured to provide a cognitive capability and thus may include a cognitive computing system that emulates a human thought process using specifically configured computing logic that is specifically configured for learning and translating patient indicators of concepts that may be specific to the particular patient. The artificial intelligence tool may comprise monitoring devices deployed in the patient's environment which monitor the patient's interactions with persons, computing devices, and/or their environment with regard to different types of patient interactions (e.g., audible, physical motions, writing or drawing, or the like). The monitoring devices, which may be separate devices in communication with or integrated with one or more computing devices deployed in the environment or remotely located, may provide input to core artificial intelligence engines that learn and interpret the input from these monitoring devices to generate associations between these inputs, referred to herein as patient indicators, and concepts during a learning phase of operation, as well as detect such inputs and respond with corresponding concepts during a runtime translation operation.

With the mechanisms of the illustrative embodiments, the artificial intelligence tool learns from the patient, such as by way of applications executing on one or more computing devices, that interact with the patient both audibly and visually, the particular patient interaction methodologies employed by the patient to convey concepts, commands, and the like. For example, the patient may, during a learning session, be exposed to particular concept stimuli, e.g., images of a concept, audible messages about the concept, or the like, and the patient's response may be monitored by the monitoring devices to capture the patient's audible responses, motion or gesture responses, or writing type responses. The patient interaction methodologies may comprise various types of patient indicators of corresponding concepts, such as particular spoken terms, phrases, sounds, etc., particular motions or gestures the patient uses to represent the concepts, and particular written terms, phrase, shapes, contours, and the like, that represent the concepts to the patient.

The artificial intelligence tool increases or "grows" its knowledge of what the patient is attempting to communicate, and the particular way in which that patient communicates, over time, i.e. what patient indicators, combinations of patient indicators, or patterns of patient indicators are used by the patient to communicate particular concepts. The artificial intelligence tool can then provide a responsive action to the patient's communication attempts, e.g., provide a visual on-screen, audible, or other output of a "translation" of the patient's verbal, physical motion or gesture, and/or writing or drawing communication for family members, caregivers, and other persons. In some illustrative embodiments, the translation of the patient's communications, i.e. the patient's indicators, may be used to control devices within the patient's environment, e.g., televisions, radios, air-conditioning units, hospital beds, devices that output notifications to caregivers or family members, or any other device or system which can be controlled by providing a user input. In still other illustrative embodiments, a direct interaction with the patient is made available by asking questions and translating answers received from the patient for use by caregivers, family members, and other persons with which the patient communicates.

There are many different ways in which the artificial intelligence tool of the illustrative embodiments may learn the patient's interaction methodologies, e.g., particular verbal and/or physical gesture-based communication methodologies and/or written methodologies in which terms, phrases, contours, shapes, or the like are used to represent the concepts. For example, in one illustrative embodiment, the artificial intelligence tool may perform one or more learning sessions with the patient by providing an output of an item representing a concept, on a display, via an audio output device, or the like, such as an image of an object/person/place/activity/feeling, etc. The artificial intelligence tool may then request that the patient identify the item displayed. The artificial intelligence tool may then listen, watch, or monitor an input device (such as a digital notepad or the like) to capture the patient's verbal response, physical motions, gestures, writings/drawings, or the like, and identify a correlation between these patient's indicators and the actual identification of the concept represented by the output of the time, also referred to herein as a concept stimulus. For example, if the artificial intelligence tool outputs a display of an image of a car, and the patient responds with an audible sound of the type "vroom, vroom" i.e. the sound that a car with its engine revved, then the artificial intelligence tool may correlate the patient's audible sound of "vroom, vroom" with the term "car," and possible synonyms or other equivalent terms for "car," e.g., automobile.

It should be appreciated that a single instance of the audible response or other patient indicator from the patient may not be sufficient to draw an actual correlation. That is, the same patient may respond differently at different times with similar prompt images or outputs by the artificial intelligence tool. Also, it is desirable to present different prompt images or outputs of the same object/person/place/activity/feeling or other concept (collectively referred to as a "concept" herein) in order to determine if the patient's response is indeed indicating the way that the patient communicates the concept or is an outlier response. Thus, it is important to determine that the patient routinely responds in the same manner to representations of the same concept in order to correlate the patient's way of communication with the particular concept, and thus, the accepted terms/phrases used to convey such concepts to others that are not afflicted with the medical condition. Such learning is performed by the artificial intelligence tool over time by performing evaluations of the responses, i.e. patient indicators, from the patient to the various concept prompts or stimuli.

Similar learning may be performed with regard to the patient's movements in response to concept prompts or stimuli. For example, if a particular movement occurs each time an item is shown on the display, then the movement may be the way that the patient is trying to communicate the corresponding concept. This may be the case when the patient is unable to speak the word for the displayed item or generate a desired audible sound to represent the item that is displayed, for example. Thus, for example, if the display screen is showing an image of a car, and the patient uses the index fingers on both hands to draw "circles" in the air, and this movement occurs each time an image of a car is displayed, or at least a predetermined number of times with a sufficient amount of frequency, then the artificial intelligence tool will understand that when the patient draws "circles" in the air with the index fingers on both hands at the same time, then the patient is referring to a car or automobile. In this case, the two circles being drawn by the patient in the air are likely the patient connecting the idea of the car's wheels moving in circles while the car is being driven. Similar learning may also be performed with regard to written type inputs from the patient, e.g., contours, shapes, words/phrases, etc. with a digital notepad or other user input device being used to capture the patient's input.

The learning by the artificial intelligence tool may further be augmented by manual input when a family member, caregiver, or other person recognizes a correlation between a concept and the patient's interaction methodology associated with that concept, i.e. particular patient indicators such as an audible sound or motion that the patient exhibits. For example, after interacting with the patient over a period of time, a family member or caregiver may identify an association of the patient saying "hot, hot" and the action of turning down the volume of the television, the radio, or the like. Thus, the human caregiver or family member may determine that, to the patient, the phrase "hot, hot" means "turn the volume down." This correlation may be input manually by the caregiver or family member into the artificial intelligence tool by specifying the mapping of the patient's phrase to the meaning "turn the volume down", which in turn may also be mapped to particular controls for devices within the patient's environment, as discussed hereafter.

It should be appreciated that the learning of associations between sounds, terms, phrases used by the patient, and/or motions or actions performed by the patient, may be performed with regard to any type of sounds, terms, phrases, motions, actions, or other patient indicators. For example, the patient may use neologisms or paraphasia terms which are recognized by the artificial intelligence tool of the illustrative embodiments and correlated with concepts, terms/phrases representative of the concepts, and in some cases, controls for controlling devices within the patient's environment. A neologism is a made-up word, such as when a person utters "skucker" when he/she is really trying to say "cook." Thus, skucker can be recognized by the artificial intelligence tool of the illustrative embodiments and mapped to the concept and term "cook." In some cases, such mapping may further map to a particular control, such as turning on a microwave or starting the oven, which may be implemented using wired or wireless computerized communication technology via which commands may be issued to devices which are able to understand the commands and perform corresponding actions. A paraphasia is a similar sounding term, such as when a person says "sook" or "look" but is really trying to say "cook." Thus, again, the term "sook" may be learned by the artificial intelligence tool to map to the concept and term "cook" as well as any mapped controls of devices in the patient's environment. For more information about such types of aphasia, reference is made to the Aphasia Center website at theaphasiacenter.com and in particular, the article entitled "What is Wernicke's Aphasia?" published Jan. 28, 2012.

It should be appreciated that the interactions or communications performed by the patient, which are recognizable by the artificial intelligence tool of the illustrative embodiments, are not limited to audible sounds and/or motions or gestures performed by the patient. As mentioned previously, in some illustrative embodiments, the interactions, or patient indicators, may be by way of written input if the patient is able to hold a writing instrument or otherwise handle an input device for purpose of writing. For example, the artificial intelligence tool of the illustrative embodiments may prompt the patient to write a specific word on a digitally-enabled notepad or other writing based input device. Thus, if the artificial intelligence tool requests that the patient write the word "car" on a digital notepad device, and the patient writes a series of curves, lines, symbols, or other contours, but failing to write specifically the letters "c", "a", and "r", then the artificial intelligence tool will know that when the patient writes something similar to the contours the patient input via the digital notepad device, the patient means "car."

It should be appreciated that the learning performed by the artificial intelligence tool of the illustrative embodiments is performed over time in order to learn the most probable associations or mappings between patient utterances, motions, written words, phrases, shapes or contours, or other types of patient indicators, and the concepts that the patient means to be conveying. For example, the patient may utilize similar patient interaction methodologies, e.g., patterns or combinations of one or more patient indicators, for multiple similar concepts and the artificial intelligence tool of the illustrative embodiments learns the nuances of the different similar patient interaction methodologies (patterns or combinations of patient indicators) and the differences between the similar concepts. Moreover, the patient's interaction methodology with regard to particular concepts may change over time and patterns between patient interactions/communications and the like with regard to concepts being conveyed may change.

For example, the patient may say "vroom, vroom" when exposed to an image of a car. The patient may also say "vroom, vroom" but with a circular hand motion when exposed to an image of a bus. In one illustrative embodiment, the patients' response may be simply associated with the particular concept, term, synonyms, etc. Thus, in this example, "vroom, vroom" would be mapped to both car and bus whereas the circular hand motion would be mapped to the concept of a bus, but not mapped to the concept of car. Furthermore, the patient may be exposed to multiple instances of stimuli representing cars, potentially with different images, different audible cues, etc., and the patient may respond the same or differently to these different stimuli. Similar responses will increase the likelihood that when the patient later attempts to communicate using the response, that the artificial intelligence tool will recognize that response, or patient indicator, as meaning the correct concept. For example, if the patient is exposed to 10 different images of a car and each time, or at least a majority of the time, the patient responds with "vroom, vroom," the artificial intelligence tool will recognize a relatively higher likelihood that when the patient later says "vroom, vroom" the patient is attempting to communicate the concept of a car. Moreover, the artificial intelligence tool may differentiate patterns of responses such that the artificial intelligence tool may determine a difference between just saying "vroom, vroom" and both saying "vroom, vroom" and making a circular motion, which is used to indicate the concept of a "bus."

Hence, the artificial intelligence tool of the illustrative embodiment may repeatedly record or collect data corresponding to the patient's interaction methodology, i.e. the patient indicators, in response to concept prompts/stimuli representing the same concept. These concept prompts/stimuli may be different from instance to instance, even though they may represent the same concept. Over time the artificial intelligence tool learns an association of the patient's interaction methodology responses, e.g., audible responses, motions or gestures, written contours, etc., with concepts and a strength or weight associated with these associations. The strength or weight of the association may be determined based on a function of a number of occurrences of the response in association with the corresponding stimuli representing the concept. Thus, for example using a simple function based on a raw percentage, if the patient is presented with an image of a car 10 times and 8 out of the 10 times the patient responds with an audible "vroom, vroom" sound, then the strength or weight of the association "vroom, vroom" with the concept "car" and its terms/synonyms may be 0.8 or 80%. The particular function used may take many different forms and may have various levels of complexity depending on the desired implementation and the particular factors that are to be included in the consideration of the strength or weight of the associations.

In some cases, the function may have a relative statistical evaluation that evaluates the relative frequency of particular patient indicators with regard to other patient indicators observed from the patient for the same concept stimuli. Using a relative measure of strength or weight of associations of patient indicators with concepts allows for dynamic modification of the strengths/weights of the associations as the patient changes their way of communicating concepts. Such changes in communication may occur for various reasons, such as slow healing which may result in better communications/cognitive over the course of years. Other possible reasons for changes in the way a patient communicates may be increases in scar tissue within the brain as the stroke is healed, which may in fact result in diminished abilities to communicate. The ability to dynamically adjust the recognition of the patient's particular manner of communicating concepts allows the illustrative embodiments to maintain an optimal level of understanding of the patient's changing communicative abilities. While some aspects of the patient's communication may improve, e.g., hand motions, others may deteriorate, e.g., speech. The mechanisms of the illustrative embodiments may promote optimal response to help improve matching of the patient's communications with the concepts the patient is attempting to communicate.

As an example of the dynamic changing of a patient's communication consider that the patient may initially use the audible response "vroom, vroom" to represent a car, but then later may change to simply using a circular motion with their finger. As the frequency of the circular motion patient indicator increases in association with the concept stimuli for the concept "car", the strength of association of "vroom, vroom" with the concept of a car may diminish while the strength of the association of the circular motion and the concept of car will increase. Moreover, a timing aspect may be included in the function to represent more recently used patient indicators as having a higher strength association than older patient indicators, thereby taking into account the changes in the way the patient communicates a concept over time.

Still further, different weighting of particular associations between patient indicators and concepts may be provided based on whether the association was determined automatically by the artificial intelligence tool, or whether the association was manually input by a human caregiver, family member, or the like. For example, greater weight or strength of association may be given to manually entered associations, or vice versa, depending on the confidence attributed to these sources of associations based on the particular implementation.

It should be appreciated that the same patient response (or patient indicator) may be associated with different concepts with potentially different strengths or weights being provided for the various associations. Thus, for example, using the above car and bus example, the patient may respond to images of the car 80% of the time by saying "vroom, vroom" and with the same amount of frequency with images of a bus. However, with images of a bus, the patient also responds with a circular motion 80% of the time as well. Thus, the artificial intelligence tool will reason that when the patient says "vroom, vroom" without a circular motion, the patient is referring to the concept of a car and when the patient says "vroom, vroom" coupled with a circular motion, then the patient is referring to the concept of a bus. It should be appreciated that these are only arbitrarily selected examples intended to illustrate the nuanced differences in patient interaction methodologies that may be identified by the artificial intelligence tool of the illustrative embodiments and are not intended to be limiting on the present invention in any way.

Thus, the artificial intelligence tool of the illustrative embodiments builds a mapping of the patient's interaction methodology, i.e. the particular patient indicators, patterns of patient indicators, or combinations of patient indicators, over time and generates for each recognizable concept, a corresponding set of patient indicators (audible, motion or gestures, written contours, etc.) that have been detected as being used by the patient in association with stimuli representing the concept. The associations between the concept and each of the patient indicators may have different strengths or weights indicative of the likelihood that the use of the patient indicator by the patient is intended to mean the corresponding concept in the association, as determined from the observations of the patient's responses to concept stimuli over time. It should be appreciated that such associations themselves may change over time and that this change in the way the patient communicates concepts may be automatically learned and represented in the strengths of associations between patient indicators and concepts.

It should also be appreciated that just as the association of a concept with one or more patient indicators is generated by the learning performed by the artificial intelligence tool, the mapping of each patient indicator to one or more concepts is also identified by the artificial intelligence tool. That is, the same patient indicator may be associated with different concepts and thus, there may be different associations of the same patient indicator with multiple different concepts, each having their own strengths of associations based on the observations made of the patient's interaction methodology. This may lead to situations, during runtime translation as discussed hereafter, where a patient generates a patient indicator, e.g., says the phrase "vroom, vroom," and the artificial intelligence system attempts to determine the most likely meaning that the patient is attempting to convey from amongst a plurality of possible concepts with which the phrase "vroom, vroom" has an association. This may take into consideration the relative strengths of associations, particular patterns or combinations of patient indicators that further define the concepts the patient is intending to convey, as well as other contextual information that may provide clues as to the more probably association for a particular situation, as will be described in greater detail hereafter.

Having performed an initial learning of the patient's interaction methodology with regard to various concepts, during runtime operation, the artificial intelligence tool of the illustrative embodiments may be employed to translate the patient indicators generated by the patient into expressions of the concept that are readily understandable by caregivers, family members, or other persons that are not afflicted by the medical condition impairing the communication capability of the patient. When the patient generates the patient indicator, either just during daily activities or when interacting with others in the patient's environment, or when specifically responding to questions presented by other persons, monitoring devices within the patient's environment may detect the patient indicator, e.g., audio and/or video capture devices, and initiate a translation action to determine what concept(s) the patient is attempting to communicate by generating the patient indicator, e.g., an audible sound, a motion or gesture, a written input, or the like. The monitoring devices generate inputs to a patient interaction system which identifies the particular patient indicator(s). The patient interaction system may utilize various tools to convert the inputs from the various monitoring devices into inputs upon which the patient interaction system may operate, e.g., voice to text conversion with natural language processing, captured image analysis used for recognizing motions or gestures, handwriting recognition applications that are used for recognizing written input, or the like.

The received patient indicator inputs, e.g., recognized terms/phrases or sounds, recognized motions or gestures, and/or recognized written shapes or contours, are provided to a cognitive patient translation system which matches the patient indicator inputs and/or patterns or combinations of the patient indicator inputs to those that have been learned for the particular patient. The cognitive patient translation system may determine that a plurality of concepts are possibly being communicated by the patient based on a degree of matching of the patient indicator input received from the monitoring devices, and the relative strengths of the associations between those matching patient indicators and concepts. An evaluation of additional contextual information may further be made to select between the potential candidate concepts that the patient is likely attempting to communicate. This contextual information may comprise temporal context information, environment context information, interaction context information, historical context information, and the like.

For example, temporal context information may comprise the particular time of day that the patient's indicator inputs are received relative to a stored schedule for the patient and/or general understanding of activities performed at different times of the day, e.g., near a mealtime, near bathing time, near bedtime, etc. The environment context information may comprise information regarding the particular section of the patient's environment in which the patient indicators were captured, e.g., in the kitchen, bathroom, living room, etc. The interaction context information may comprise information regarding the particular context of a conversation that another person is having with the patient, in which the patient generated the patient indicator. The historical context information may comprise historical information regarding previous concepts communicated by the patient at similar times of the day. Any one or a combination of two or more of these contexts may be utilized along with the degree of matching and the relative weights or strengths of associations to generate a scoring of the candidate concepts that the patient is likely attempting to communicate.

Based on the evaluation of the concepts that are potentially being communicated, one or more final concepts are selected for presentation, such as via a display device, audio output device, or the like. The one or more final concepts and their corresponding information may be sent back to the patient interaction system for presentation in the patient environment. For example, images and/or terms/phrases corresponding to the one or more final concepts may be output via a display device associated with the patient interaction system present in the patient environment for use by caregivers, family members, or other persons present in the patient environment. For example, if the patient says "hot, hot" which the artificial intelligence tool has previously learned to be the patient's way of communicating the concept of "turn down the volume," then the phrase "turn down the volume" may be displayed on a display screen and/or output in an audible format via one or more audio output devices, e.g., speakers.

It should be appreciated that in some instances, multiple final concepts may be selected for presentation, in which case the patient may be asked to identify which concept the patient intended. For example, the final concept candidates may be sequentially highlighted, and the patient asked to respond when the correct one is highlighted. Such feedback from the patient may be noted and used to further improve the learning of the artificial intelligence system by updating associations of patient indicators with concepts in the database of learned patient indicators. Thus, an ongoing dynamic learning is achieved using the mechanisms of the illustrative embodiments.

In some instances, the patient's environment may be configured with devices which may be controlled via control messages transmitted wirelessly or via wired connections, such as via a local area network of the patient's environment. Thus, when a patient's indicator is translated to a corresponding concept and that concept has an associated command or action that can be performed automatically by transmitting a control message to a corresponding device, the patient interaction system of the illustrative embodiments may send the control message to cause the automatic performance of the corresponding action. For example, in the case of the patient saying "hot, hot" and this patient indicator being translated to the concept of "turn down the volume," the patient interaction system may further determine that this concept has the associated command to turn down the volume of the television in the patient environment. As a result, a wired or wireless control message may be transmitted to the receiver on the television to cause the television to reduce the volume of the speakers of the television. Similar controls may be performed with regard to any controllable electronics in the patient environment either directly due to receivers integrated in the devices, or via external device control units that may be coupled to or otherwise associated with the devices after manufacturing, e.g., devices for enabling smart home functionality such as turning on/off lights, locking doors, changing the color of lights, or otherwise controlling any of a variety of different devices within the patient environment.

As discussed above, the patient may be monitored in the patient environment to determine if the patient generates a patient indicator that is to be translated by the artificial intelligence mechanism of the illustrative embodiments. This monitoring can be performed on a continual basis in some illustrative embodiments by using the monitoring devices to capture inputs from the environment and analyzing the inputs to determine if they match any known patient indicator. In other illustrative embodiments, the monitoring may be initiated in response to a trigger input, e.g., a trigger word or phrase being uttered in the patient environment, a particular motion or gesture being detected, or other input initiated by a human being present in the patient environment (the patient or another person present), e.g., the patient pressing a "help" button on a wearable device. For example, in one illustrative embodiment, the patient may speak the word "lelp" in order to initiate the operation of the patient interaction system. As the cognitive patient translation system of the illustrative embodiments has learned that this patient's statement "lelp" corresponds to a request for "help", the patient interaction system may be prompted to respond in a conversational manner automatically by outputting a message "how may I help you?" and then listening/watching with the monitoring devices present in the patient environment to detect patient indicators. Alternatively, the cognitive patient translation system may automatically send a message to a caregiver or family member indicating that the patient has requested help. In the former case, where patient indicators are detected using the monitoring devices, the patient indicators may be translated in the manner discussed above and a corresponding output and/or control message may be generated so as to provide the assistance that the patient needs and/or enlist the assistance of a caregiver, family member, or other person.

Thus, the illustrative embodiments provide mechanisms for assisting patients with diminished cognitive capabilities with communicating with other human beings and/or interacting with their environment. The illustrative embodiments recognize the particular personalized way in which a patient with such diminished capabilities communicates concepts and translates those communications into a form that is recognizable by others that do not suffer from such diminished capabilities. Moreover, in some illustrative embodiments, the mechanisms provide automated interaction with devices in the patient environment so as to control them in accordance with the translated communications from the patient.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for learning the personalized way in which a patient with diminished cognitive and/or communication capabilities, such as due to a brain injury, stroke, or the like, communicates concepts. Based on the learning, translation functionality is provided for translating the patient's indicators into concepts that human caregivers, family members, and other persons are able to recognize. Moreover, in some cases, automatic controls may be enabled for controlling devices in the patient's environment based on the translated concepts. The illustrative embodiments utilize specially configured artificial intelligence and cognitive computing systems to facilitate the learning and translation capabilities. The result is that patients that previously had difficulty communicating with others and/or interacting with their environment are afforded greater communication capability and interaction capability, thereby improving their lifestyle and relationships with others. This in turn may increase the ability of caregivers and family members to provide better care due to the increased ability to understand and communicate with the patient and knowing the patient's needs.

Figure 2:
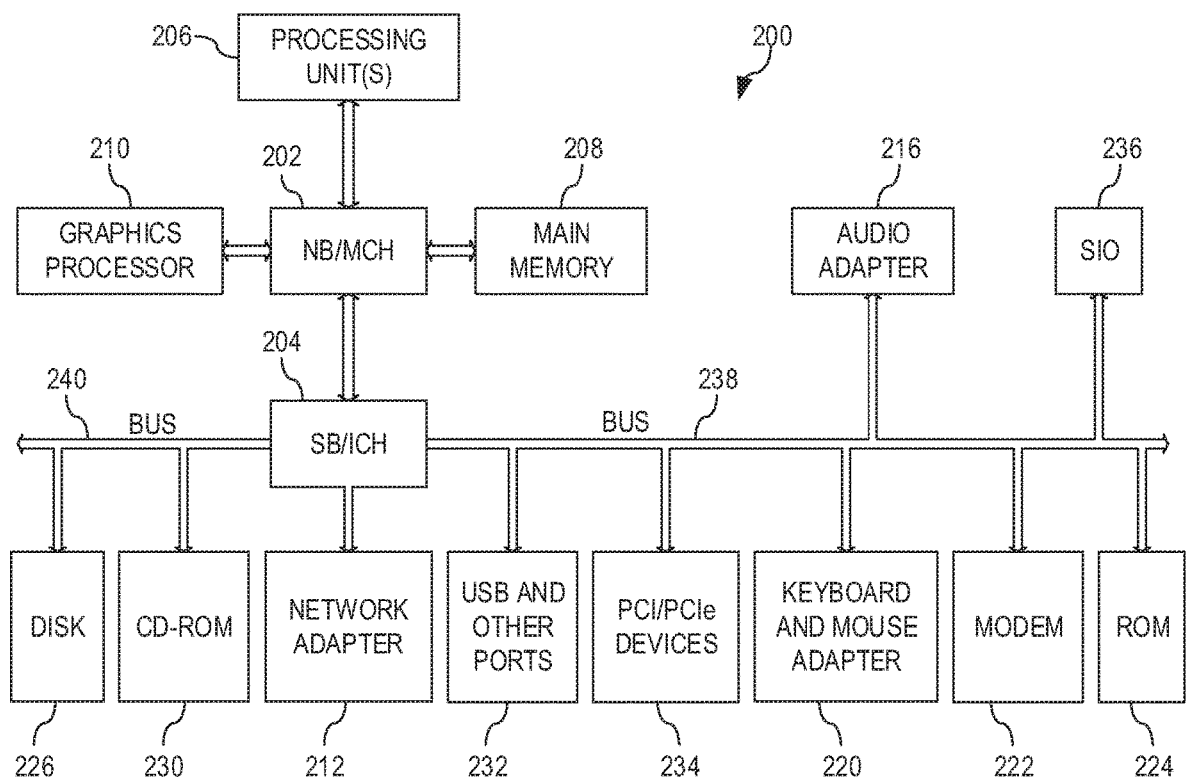
FIG. 2 is a block diagram of an example data processing system in which aspects of the illustrative embodiments are implemented.
Figure 3:
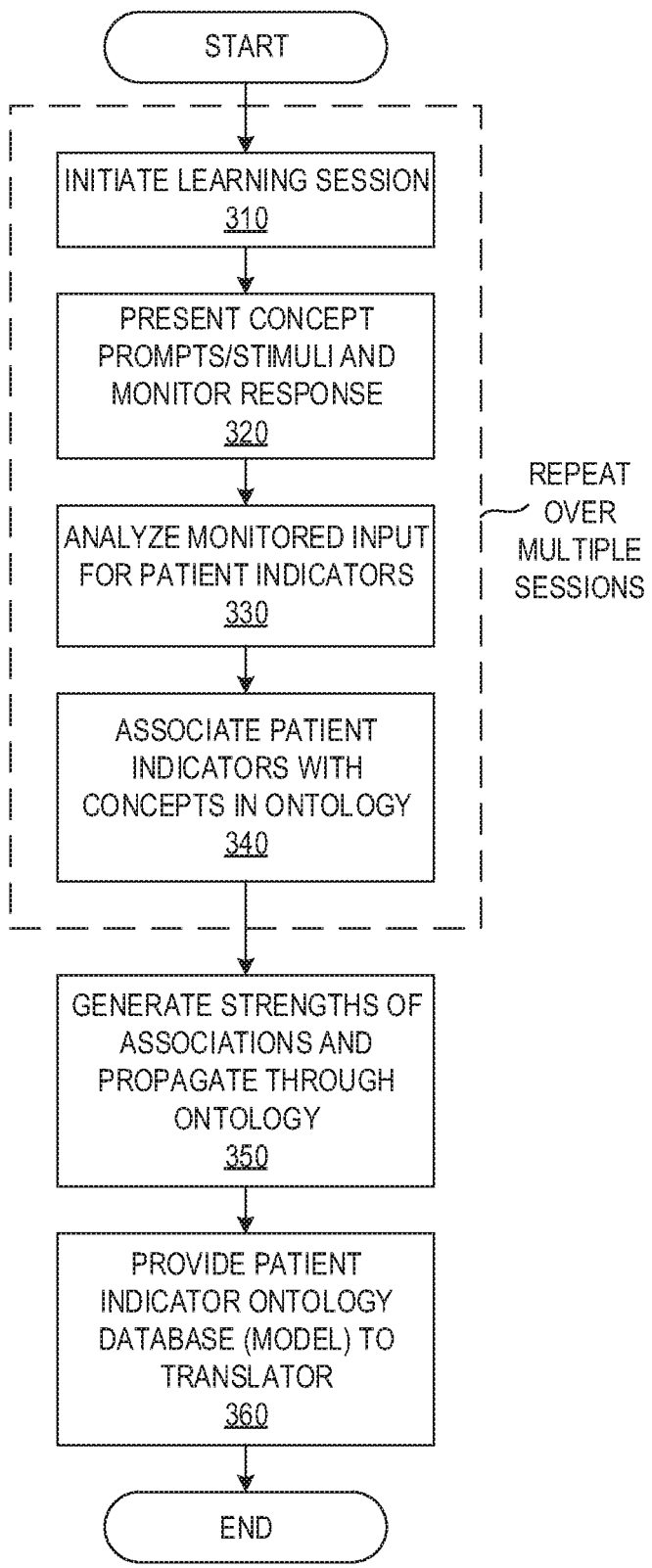
FIG. 3 is an example flowchart outlining an operation for learning patient indicators and their associations with concepts in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIG. 1 is an example block diagram illustrating an example of the primary operational elements of one illustrative embodiment and their interactions for facilitating learning and translation of patient indicators. As shown in the example illustrative embodiment of FIG. 1, a patient interaction system 110 is provided in a patient environment 102. The patient interaction system 110 may comprise a computing device specifically configured to received inputs from monitoring devices 112-114 which may be deployed in the patient environment 102, identify patient indicators in the received inputs, and learn/translate such patient indicators using the cognitive or artificial intelligence capabilities of a cognitive patient translation system 120. The patient interaction system 110 may receive inputs from the monitoring devices 112-114 and may communicate with the patient and/or other persons in the patient environment 102 via output devices 116 which may comprise visual output devices (e.g., display devices), audio output devices (e.g., speakers), and the like. Although not explicitly shown, other patient input devices may also be utilized, such as digital notepads, which may provide inputs to the patient interaction system 110 which may be processed to identify patient indicators.

In the depiction of FIG. 1, the cognitive patient translation system 120 is a remotely located computing system specifically configured to implement a cognitive computing functionality that is specifically concerned with learning and translating patient indicators into concepts and/or corresponding commands to assist the patient in communicating with other persons and with interacting with the patient environment 102. It should be appreciated that while FIG. 1 shows the cognitive patient translation system 120 as a remotely located computing system, the illustrative embodiments are not limited to such. To the contrary, the cognitive patient translation system 120 may be integrated with the patient interaction system 110 in the patient environment 102. In a remotely located embodiment, the cognitive patient translation system 120 may be in communication with the patient interaction system 110 via one or more networks 104.

During a learning phase of operation, the cognitive patient translation system 120 may communicate with the patient interaction system 110 to interact with the patient 100 to present prompts and receive patient responses comprising patient indicators that may be learned by the cognitive patient translation system 120. It should be appreciated that such learning may be performed over multiple learning phases over time. For example, a learning phase schedule may be established whereby the patient is asked to interact with the patient interaction system 110 for a predetermined amount of time on a regular basis, e.g., an hour per day for a predetermined number of days, to provide patient responses to prompts for purposes of training the cognitive patient translation system 120 via a learning operation. During the learning phase of operation, the patient is presented with prompts, e.g., visual or audio prompts, and the patient's response is monitored by the monitoring devices 112-114 to thereby identify the patient's response as a patient indicator.

For example, the patient interaction system 110 may display via the output device 116 an image of a concept, e.g., a car, food, bathroom, television, medicine, etc., such as a concept associated with a daily need of the patient. The patient may then be asked what the image is, and the patient may respond using the communication methodology used by the patient to convey the meaning of the concept, e.g., saying "vroom, vroom" or "hot, hot", making a motion or gesture, and/or writing a shape, contour, letters, words, or phrases on a digital notepad, or the like.

The patient's responsive interaction comprising the patient indicator(s) of the concept specified in the prompt or stimulus, e.g., the image related to the concept, is recorded by the monitoring devices 112-114 and provided to the patient interaction system 110 which correlates the characteristics of the patient indicator(s) with the identification of the concept corresponding to the prompt or stimulus. Thus, for example, if the patient interaction system 110 outputs an image of a car, and the patient responds with "vroom, vroom", then the term "vroom, vroom" is associated with the concept of a car. If the patient interaction system 110 outputs an audio sound that is very loud and the patient responds "hot, hot" followed by the audio sound volume being reduced by the patient interaction system 110 and the patient responding positively (e.g., shaking head "yes" or saying "yes") then the term "hot, hot" may be associated with the action to "turn down the volume." If the patient interaction system 110 outputs an image of a food item, and the patient responds by making a gestured directed to the patient's mouth, e.g., placing a finger on the patient's lip, then that gesture may be associated with the concept of food, eating, and/or hungry.

The associations of patient indicators with concepts may be provided by the patient interaction system 110 to a concept/indicator learning engine 122 of the cognitive patient translation system 120 which associates the characteristics of the patient indicator(s) with the concepts and/or their related concepts and/or characteristics. For example, if the patient responds to an image of food with both a hand gesture to the patient's mouth and a clicking sound, then both patient indicators may be associated with the concept of food. Moreover, the concept of food may have multiple related concepts such as eating, hungry, meal, etc. and the patient indicators may be further associated with these related concepts as well. Over time, after a plurality of learning sessions have occurred, each concept and related concept will have its own associated sets of patient indicators and the frequency of occurrence of these patient indicators in association with these concepts, i.e. how often the patient has responded to a prompt or stimulus related to the concept during learning sessions over time. These frequencies of occurrence may be used to generate a strength or weight of association between the patient indicators and the various concepts in a patient indicator ontology database 124.

As mentioned previously above, the learning performed by the concept/indicator learning engine 122 of the cognitive patient translation system 120 may further be augmented by manual input when a family member, caregiver, or other person recognizes a correlation between a concept and particular patient indicators, such as an audible sound or motion that the patient exhibits when prompted or provided stimuli related to the concept. The correlation may be input manually by the caregiver or family member into the concept/indicator learning engine 122 via the patient interaction system 110 in the patient environment 102 by specifying the mapping of the patient's indicator to the concept, e.g., mapping the term "hot, hot" with the concept of "turn down the volume," which in turn may also be mapped to particular controls for devices within the patient's environment, as mentioned above.

As mentioned above, the learning performed by the concept/indicator learning engine 122 is performed over time in order to learn the most probably associations or mappings between patient utterances, motions, written words, phrases, shapes or contours, or other types of patient indicators, and the concepts that the patient means to be conveying. For example, the patient may utilize similar patient interaction methodologies, e.g., patterns or combinations of one or more patient indicators, for multiple similar concepts and the artificial intelligence tool of the illustrative embodiments learns the nuances of the different similar patient interaction methodologies (patterns or combinations of patient indicators) and the differences between the similar concepts. Moreover, the patient's interaction methodology with regard to particular concepts may change over time and patterns between patient interactions/communications and the like with regard to concepts being conveyed may change.

Hence, the concept/indicator learning engine 122 of the illustrative embodiments may repeatedly record or collect data corresponding to the patient's interaction methodology, i.e. the patient indicators, in response to concept prompts/stimuli representing the same concept, as it is collected by the patient interaction system 110 during learning sessions with the patient 100. These concept prompts/stimuli may be different from instance to instance, even though they may represent the same concept. Over time, the concept/indicator learning engine 122 generates associations association of the patient's interaction methodology responses, e.g., audible responses, motions or gestures, written contours, etc., with concepts in an ontology of concepts. The ontology of concepts represents concepts recognizable by the cognitive patient translation system 120 and may represent relationships between concepts. A general ontology data structure representing generally recognizable concepts and their relationships may be used as a basis for generating individual patient instances of this ontology data structure, such as patient indicator ontology database 124, which encapsulates not only the general ontology, but the learned associations of patient indicators with the concepts of the ontology.

The concept/indicator learning engine 122 may operate on the general ontology data structure to record the collected data corresponding to the patient interaction methodology in association with the concepts corresponding to the particular prompt or stimuli. The associations of patient indicators in the patient interaction methodology with the concepts may be used as a basis for generating a strength or weight value associated with these associations between patient indicator and concept. The strength or weight of the association may be determined based on a function of the frequency of occurrences of the patient indicator in association with the corresponding stimuli representing the concept, as previously discussed above. The particular function used may take many different forms and may have various levels of complexity depending on the desired implementation and the particular factors that are to be included in the consideration of the strength or weight of the associations. In some cases, the function may have a relative statistical evaluation that evaluates the relative frequency of particular patient indicators with regard to other patient indicators observed from the patient for the same concept stimuli. In some implementations, a timing aspect may be included in the function to represent more recently used patient indicators as having a higher strength association than older patient indicators, thereby taking into account the changes in the way the patient communicates a concept over time. Still further, different weighting of particular associations between patient indicators and concepts may be provided based on whether the association was determined automatically by monitoring the patient in the patient environment 102 using the monitoring devices 112, 114 and the patient interaction system 110, or whether the association was manually input by a human caregiver, family member, or the like, e.g., since there may be more potential error in the automated mechanism due to limitations in the way that computing devices interpret human communication, a lower relative weight may be associated with automated associations as opposed to human manually entered associations which may be given a relatively greater weight in the function used to generate the strength/weight values for the associations.

The strength/weight values generated by the concept/indicator learning engine 122 based on the particular implemented function and the observations of patient indicators in association with concept prompts/stimuli may be associated with nodes in the patient indicator ontology database 124. In some illustrative embodiments, a propagation of the learning may occur in accordance with the ontology so that, according to desired propagation rules, various amounts of the strengths/weights may be associated with related concepts as indicated in the ontology. For example, the ontology may be a hierarchical arrangement of concepts with parent concepts having related child concepts that may inherit a portion of the strength/weight of the parent concept, or vice versa, according to propagation rules. In general, the parent concept should be a more general concept while the child concepts are more specific to particular situations. Thus, for example, if a particular patient indicator is associated with the concept of eating, the strength of the association of that parent indicator with the concept of eating may be propagated to child concept nodes in the ontology, such as food, meals, hungry, etc. according to the propagation rules. The propagation rules may not simply attribute the full strength of association to the child concepts and instead may propagate a portion of the strength according to a distance between nodes in the ontology representing the concepts, e.g., a number of edges between nodes needed to reach the child node. The more distant a node is from the parent node, the smaller the amount of the strength of association value is propagated to that node. Thus, while there may be a 90% strength of association between the patient indicator of a hand to the patient's lips with the concept of eating, perhaps only a 30% strength of association between that patient indicator and the concept of "food" is propagated to the node representing the concept of food in the patient indicator ontology database 124, in accordance with the particular propagation rules employed.

It should be appreciated that the same patient response (or patient indicator) may be associated with different concepts with potentially different strengths or weights being provided for the various associations. This may be due to the propagation discussed above or the fact that the patient actually uses the same patient indicator to represent different concepts, e.g., the patient may utilize the phrase "vroom, vroom" with both the concept of a car and the concept of leaving the patient environment 102 (such as for a car ride). Thus, multiple nodes in the patient indicator ontology database 124 may comprise the same patient indicators but potentially with different strengths or weights of association. This may then lead to multiple matches or "hits" when the cognitive patient translation system 120 later is attempting to translate the patient's communications during runtime operation as mentioned previously.

Thus, during the learning phase of operation, the concept/indicator learning engine 122, over multiple learning sessions, builds an understanding of how the particular patient 100 communicates concepts by learning the associations between the patient indicators, e.g., audible utterances, motions or gestures, writing of shapes, contours, and the like, and the particular concepts. The concept/indicator learning engine 122 further learns the strengths of associations between the patient indicators and the concepts, and may utilize an ontology and propagation rules to provide a more intelligent learning of how the patient communicates.

Having performed an initial learning of the patient's interaction methodology, i.e. the set of patient indicators used by the patient to communicate concepts, during runtime operation, the runtime translation engine 126 of the cognitive patient translation system 120 may be employed to translate the patient indicators generated by the patient into expressions of the concept that are readily understandable by caregivers, family members, or other persons. The patient 100 may generate patient indicators either just during daily activities, when interacting with others in the patient's environment 102, or when specifically responding to questions presented by other persons. The patient 100 may also initiate detection of patient indicators by providing a trigger input that is detected by the monitoring devices 112, 114, such as saying a trigger term, sound, or the like, performing a trigger motion or gesture, or writing a trigger shape, contour, or term/phrase on a digital notebook, or the like. For example, the patient may trigger the detection by saying the word "help" or other sound that the patient knows triggers a response from the patient interaction system 110.

Either continuously, or in response to the trigger input, the monitoring devices 112, 114 within the patient's environment 102 may detect one or more patient indicators of concepts that the patient is attempting to communicate, and initiate a translation action. The monitoring devices 112, 114, again generate inputs to the patient interaction system 110 which identifies the particular patient indicator(s) present in the inputs. As during the learning phase of operation above, the patient interaction system 110 may utilize various tools to convert the inputs from the various monitoring devices 112, 114 into inputs upon which the patient interaction system may operate, e.g., voice to text conversion with natural language processing, captured image analysis used for recognizing motions or gestures, handwriting recognition applications that are used for recognizing written input, or the like.

The received patient indicator inputs are provided by the patient interaction system 110 to the cognitive patient translation system 120, potentially via one or more networks 104. The cognitive patient translation system 120 matches the patient indicator inputs and/or patterns or combinations of the patient indicator inputs to those that have been learned for the particular patient and are stored in the patient indicator ontology database 124. That is, the runtime translation engine 126 of the cognitive patient translation system 120 the cognitive patient translation system 120 may traverse the patient indicator ontology database 124 to identify nodes for which there are matching patient indicators and then compile a listing of these matching nodes. This listing may comprise the identification of the nodes as well as the matching patient indicators and their strengths of association with the corresponding concepts represented by the nodes, for example. In some illustrative embodiments, a fuzzy matching may be made possible where the patient indicator may have various degrees of matching with the particular indicator or pattern/combination of indicators associated with a node, e.g., the patient indicators match one of the patient indicators of the node, but not all of the patient indicators in a pattern/combination associated with the node.

Based on the matching, the runtime translation engine 126 of the cognitive patient translation system 120 may determine that a plurality of concepts are possibly being communicated by the patient based on the degree of matching of the patient indicator input received from the monitoring devices 112, 114, and the relative strengths of the associations between those matching patient indicators and concepts. The runtime translation engine 126 may make an evaluation of additional contextual information 128 in order to select between the potential candidate concepts that the patient is likely attempting to communicate. This contextual information may comprise temporal context information, environment context information, interaction context information, historical context information, and the like.

As noted above, temporal context information may comprise the particular time of day that the patient's indicator inputs are received relative to a stored schedule for the patient and/or general understanding of activities performed at different times of the day, e.g., near a mealtime, near bathing time, near bedtime, etc. Thus, for example, timestamp information may be associated with the received patient indicators which indicates the time of day that the patient indicators were detected or received. Alternatively, a current time may be used since the system is designed to be readily responsive to the patient's indicators so as to respond to patient needs. The time context information may be correlated with generally known information about how people conduct their lives on a daily basis, and/or particular knowledge for the particular patient, e.g., when this particular patient engages in different activities. For example, the knowledge may be represented in a predetermined patient schedule which may be stored in the cognitive patient translation system 120 and used as contextual information for evaluating the candidate concepts corresponding to the patient indicators.

Thus, for example, assume that there are two candidate concepts that match the patient indicator. One of the candidate concepts is associated with eating and the other is associated with a bed time. If the patient indicator is received at a time that is closer to bed time than to a meal time in the patient's personal schedule, then the candidate concept corresponding to the bed time will be given a higher evidential score ranking than the candidate concept associated with eating, as it is more likely that the patient is attempting to communicate the concept associated with bed time than with meal time. This may be reversed if the timing is closer to meal time than bed time. Of course, this is a relative evaluation and thus, there will be times where neither candidate concept has a clearly higher evidential scoring, in which case the score may be unchanged based on temporal context information.

The environment context information may comprise information regarding the particular section of the patient's environment in which the patient indicators were captured, e.g., in the kitchen, bathroom, living room, etc. Again, using the example above, if the patient's environment 102 comprises a plurality of locations having different known characteristics, this information may be maintained by the cognitive patient translation system 120 in association with the patient. Moreover, the particular monitoring devices 112, 114 and the locations where they are deployed within the patient environment may be registered with the cognitive patient translation system 120 and maintained therein for use as evidential context information. Thus, if a patient indicator is detected from an input from a monitored device 112 deployed in a bedroom of the patient's environment 102, then it is more likely that the patient is attempting to communicate a concept associated with bed time than if the patient were in the kitchen, dining room, or even living room, where it may be more likely that the patient is attempting to communicate a concept associated with eating or meal time.

The interaction context information may comprise information regarding the particular context of a conversation that another person is having with the patient, in which the patient generated the patient indicator. That is, the cognitive patient translation system 120 may maintain a temporary history of a conversation being conducted between the patient 100 and another person present in the patient's environment 102. The temporary history may be maintained for a predetermined time period representative of a typical conversation with terms/phrases and/or previous translations of patient indicators to concepts being used as contextual information for providing evidential support for candidate concepts. For example, the temporary history may provide an indication of the general topics being covered during the conversation to determine what the patient and the other party are communicating about. Thus, if the patient has previously been providing patient indicators that are translated to concepts that, within a patient indicator ontology database 124 are associated with a general concept of eating, then most likely the present patient indicator is concerned with eating as well. If the other party in the conversation is using terms regarding food, meals, nutrition, etc., then this is indicative that the conversation has to do with eating and thus, the patient indicator is more likely associated with eating than other concepts. Thus, this information may be used to provide higher contextual evidence for a candidate concept associated with eating as opposed to the candidate concept associated with bedtime, for example.

The historical context information may comprise historical information regarding previous concepts communicated by the patient at similar times of the day. That is, similar to the temporal context information discussed above, the historical context information may indicate patterns of concepts that the patient wishes to communicate on a regular basis. This may not be reflected in a predetermined schedule or general understanding of how most people conduct their daily lives, and may be specific to the particular patient. For example, the patient may want to watch the same television program every day and thus, may communicate at a similar time every day that they want the television turned on/off by providing a corresponding patient indicator. Thus, on a subsequent day, a communication from the patient having a patient indicator that matches multiple candidate concepts, one of which is associated with turning on/off the television, may be evaluated based on the historical context information to differentiate between these candidate concepts and give a higher evidential scoring to the candidate concept associated with turning on/off the television.

Any one or a combination of two or more of these contexts may be utilized along with the degree of matching and the relative weights or strengths of associations to generate a scoring of the candidate concepts that the patient is likely attempting to communicate.

The runtime translation engine 126 may employ a cognitive processing pipeline to perform cognitive evaluation of the patient indicators relative the patient indicator ontology database 124 and a cognitive analysis of the other contextual information which may operate as evidential input for scoring candidate concepts. That is, the patient indicator ontology database 124 may be provided as a corpus of information that is fed into the cognitive processing pipeline for processing, while the patient indicators captured by the monitoring devices 112, 114 and provided to the cognitive patient translation system 120 by the patient interaction system 110 may be received as an input request, i.e. a request that these patient indicators be translated. The cognitive processing pipeline may then process the request via multiple stages of processing as will be described hereafter, including generating queries that are applied against the corpus, e.g., the patient indicator ontology database 124, to generate candidate concepts which are then evaluated based on evidence, e.g., the contextual information for the current situation under which the patient indicators were captured, to thereby generate a ranked listing of candidate concepts that the patient is likely attempting to communicate.

Based on the evaluation of the concepts that are potentially being communicated via the pipeline of the runtime translation engine 126, one or more final concepts are selected for presentation, such as via a display device, audio output device, or the like, associated with the patient interaction system 110, e.g., output device(s) 116. The one or more final concepts and their corresponding information may be sent back to the patient interaction system 110 for presentation in the patient environment 102, such as via the output device(s) 116. For example, images and/or terms/phrases corresponding to the one or more final concepts may be output via a display device associated with the patient interaction system 110 present in the patient environment 102 for use by caregivers, family members, or other persons present in the patient environment. Thus, if the patient says "hot, hot" then the phrase "turn down the volume" may be displayed on a display screen and/or output in an audible format via one or more audio output devices, e.g., speakers, based on the previous learning of the association of the patient indicator "hot, hot" with the phrase "turn down the volume" and the evaluation of the learned associations by the runtime translation engine 126.

As noted above, in some cases a dynamic learning capability is made possible by requesting feedback from the patient when the runtime translation engine 126 generates a response to the patient indicators. For example, if multiple final concepts are selected for presentation, such as in a ranked listing or ranked output, the patient may be asked to identify which concept the patient intended, such as by highlighting the various concept candidates and requesting that the patient respond when the correct one is highlighted or indicate ones that are not correct by shaking their head "no" or the like. Such feedback from the patient may be captured by the monitoring devices 112, 114 and the patient interaction system 110 and used to further improve the learning of the artificial intelligence system by updating associations of patient indicators with concepts in the patient indicator ontology database 124 for the particular patient 100.

In some instances, the patient's environment 102 may be configured with devices 118, 119 which may be controlled via control messages transmitted wirelessly or via wired connections, such as via a local area network of the patient's environment 102 (not shown). Thus, when a patient's indicator is translated to a corresponding concept and that concept has an associated command or action specified in the patient indicator ontology database 124 that can be performed automatically by transmitting a control message to a corresponding device, the patient interaction system 110 of the illustrative embodiments may send the control message to cause the automatic performance of the corresponding action. For example, in the case of the patient 100 saying "hot, hot" and this patient indicator being translated by the runtime translation engine 126 to the concept of "turn down the volume" in the patient indicator ontology database 124, the patient interaction system 110 may further determine that this concept has the associated command specified in the node of the ontology 124 to turn down the volume of the television, e.g., device 118, in the patient environment 102. As a result, a wired or wireless control message may be transmitted to the receiver on the television 118 to cause the television 118 to reduce the volume of the speakers of the television 118. This may be repeated as long as the patient 100 continues to provide the patient indicator. Similar controls may be performed with regard to any controllable electronics in the patient environment either directly due to receivers integrated in the devices 118, 119, or via external device control units that may be coupled to or otherwise associated with the devices 118, 119 after manufacturing, e.g., devices for enabling smart home functionality such as turning on/off lights, locking doors, changing the color of lights, or otherwise controlling any of a variety of different devices within the patient environment.

It should be noted that while FIG. 1 depicts the operational elements with the cognitive patient translation system 120 operating in conjunction with a single patient interaction system 110 deployed in a single patient environment, the illustrative embodiments are not limited to such. Rather, in some illustrative embodiments, the cognitive patient translation system 120 may support a plurality of patient interaction systems 110 deployed in a plurality of different patient environments associated with a plurality of different patients. Moreover, the cognitive patient translation system 120 may be implemented on more than one computing device, such as across a plurality of server computing devices, in a cloud computing environment, or the like. The depiction presented in FIG. 1 is for simplicity and ease of understanding.

In an illustrative embodiment where the cognitive patient translation system 120 services multiple different patient interaction systems 110 for a plurality of different patients 100 and/or patient environments 102, the cognitive patient translation system 120 may maintain a plurality of different patient indicator ontology databases 124, each being associated with a different patient and having different associations of patient indicators with concepts as well as strengths of such associations depending on the particular way in which that patient communicates concepts. Thus, each patient is provided with their own customized patient indicator ontology database 124 representing their own personal way of communicating concepts. These different databases 124 are each learned using a process such as described previously, but with regard to each individual patient separate and distinct from the learning performed for other patients.

The runtime translation engine 126 will operate on the particular patient's patient indicator ontology database 124 thereby generating results that are specific to the particular patient. Moreover, in some illustrative embodiments, the particular context information that the runtime translation engine 126 utilizes to perform an evidential evaluation of the candidate concepts may be specific to the particular patient as well, e.g., the patient's own personal schedule, the patient's own personal previous history of communications, etc. Thus, a personalized cognitive evaluation of the patient's attempts at communication, i.e. the patient's indicators, is performed by the cognitive patient translation system 120.

As mentioned above, in some illustrative embodiments, the runtime translation engine 126 may implement a cognitive processing pipeline 128 to perform the operation of translating a patient's indicator(s) into an expression of a concept where that expression is more recognizable to individuals that do not suffer from the cognitive affliction that the patient has. One type of cognitive processing pipeline 128 with which the mechanisms of the illustrative embodiments may be utilized is a Question Answering (QA) pipeline or request processing pipeline, such as the processing pipeline provided in the IBM Watson™ cognitive system. It should be appreciated that while the present invention may be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What does patient P mean by "hot, hot"?", the cognitive system may instead receive a request of "translate "hot, hot" for patient P" or the like. It should be appreciated that this request may not be posed as a natural language request but instead may be simply an implicit request to process the input by executing a translation operation.

As the cognitive patient translation system 120 may be implemented as a cognitive computing system, implemented on one or more server computing devices of a distributed data processing network, it is important to first have an understanding of how cognitive systems implementing a QA or request processing pipeline are implemented before describing how the mechanisms of the illustrative embodiments are integrated in such cognitive systems and request processing pipeline, or QA pipeline, mechanisms. It should be appreciated that the mechanisms described herein are only examples and are not intended to state or imply any limitation with regard to the type of cognitive system mechanisms with which the illustrative embodiments are implemented. Many modifications to the example cognitive system shown in the figures may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

It should be appreciated that while a cognitive system may attempt to emulate human thought processes, the algorithms, operations, and configurations of the cognitive system are not the same as a human brain due to the fact that computing devices simply do not have the same architecture as a human mind and operate in a completely different way fundamentally, requiring specific configurations and logic that perform operations that a human brain does not perform, in order to emulate the results that a human brain generates. In other words, computers are not human brains, currently there is no complete understanding of how human brains operate, and thus, the human thought processes themselves cannot be duplicated, but only emulated and approximate via completely different mechanisms present in computing devices.

IBM Watson™ is an example of a cognitive system which can process human readable language and identify inferences between text passages with human-like high accuracy at speeds far faster than human beings and on a larger scale. In general, such cognitive systems are able to perform the following functions: (1) Navigate the complexities of human language and understanding; (2) Ingest and process vast amounts of structured and unstructured data; (3) Generate and evaluate hypothesis; (4) Weigh and evaluate responses that are based only on relevant evidence; (5) Provide situation-specific advice, insights, and guidance; (6) Improve knowledge and learn with each iteration and interaction through machine learning processes; (7) Enable decision making at the point of impact (contextual guidance);

(8) Scale in proportion to the task; (9) Extend and magnify human expertise and cognition; (10) Identify resonating, human-like attributes and traits from natural language; (11) Deduce various language specific or agnostic attributes from natural language; (12) High degree of relevant recollection from data points (images, text, voice) (memorization and recall); (13) Predict and sense with situational awareness that mimic human cognition based on experiences; and (14) Answer questions based on natural language and specific evidence.

In one aspect, cognitive systems provide mechanisms for answering questions posed to these cognitive systems using a Question Answering pipeline or system (QA system) and/or process requests which may or may not be posed as natural language questions. The QA or request processing pipeline or system is an artificial intelligence application executing on data processing hardware that answers questions or processes requests pertaining to a given subject-matter domain presented in natural language. The QA or request processing pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA or request processing pipeline. The document may include any file, text, article, or source of data for use in the cognitive system. For example, a QA or request processing pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the cognitive system which implements the QA or request processing pipeline. The QA or request processing pipeline then answers the input questions or responds to the requests using the content in the corpus of data by evaluating documents, sections of documents, portions of data in the corpus, or the like. When a process evaluates a given section of a document for semantic content, the process can use a variety of conventions to query such document from the QA or request processing pipeline, e.g., sending the query to the QA or request processing pipeline as a well-formed question or request which is then interpreted by the QA or request processing pipeline and a response is provided containing one or more answers to the question or a result of the request. Semantic content is content based on the relation between signifiers, such as words, phrases, signs, and symbols, and what they stand for, their denotation, or connotation. In other words, semantic content is content that interprets an expression, such as by using Natural Language Processing.

The QA or request processing pipeline receives an input question or request, parses the question to extract the major features of the question, uses the extracted features to formulate queries, and then applies those queries to the corpus of data. Based on the application of the queries to the corpus of data, the QA or request processing pipeline generates a set of hypotheses, or candidate answers/responses to the input question or request, by looking across the corpus of data for portions of the corpus of data that have some potential for containing a valuable response to the input question/request. The QA or request processing pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question or request based on the specific area of focus of that reasoning algorithm. Each resulting score is then weighted against a statistical model. The statistical model captures how well the reasoning algorithm performed at establishing the inference between two similar passages for a particular domain during the training period of the QA or request processing pipeline. The statistical model is used to summarize a level of confidence that the QA or request processing pipeline has regarding the evidence that the potential response, i.e. candidate answer, is inferred by the question. This process is repeated for each of the candidate answers/responses until the QA or request processing pipeline identifies candidate answers that surface as being significantly stronger than others and thus, generates a final answer/response, or ranked set of answers/responses, for the input question/request.

In the context of the illustrative embodiments of the present invention, the corpus operated on by the QA or request processing pipeline may be the learned patient indicator ontology database 124, with the pipeline operating on an input "question" in the form of one or more patient indicator(s) captured by monitoring devices in the patient environment, with the implicit request to translate the patient indicator(s). The "question" or request may include an identifier of the particular patient for which the translation is requested, such as by way of an indicator of the patient interaction system 110 supplying the patient indicator(s) or other identification of the particular patient. The supporting evidence that may be evaluated by the QA or request processing pipeline may include contextual information as discussed above, which may be specific to the particular patient as well. Moreover, the candidate answers or responses generated may comprise candidate translations of the patient indicators to particular concepts being communicated by the patient, which may be ranked according to the learned strengths of association between patient indicators and concepts as set forth in the patient indicator ontology database, as well as evaluation of the contextual information, to thereby generate a ranked scoring of the candidate concepts being communicated by the patient. The resulting ranked scoring may be used to provide an output in the patient environment for use by caregivers, family members, or other persons in understanding what the patient is communicating, and may be used to automatically control devices within the patient environment.

As is evident from the above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as a server or client computing device, in which computer usable code or instructions implementing the processes for illustrative embodiments of the present invention are located. For example, a data processing system such as depicted in FIG. 2 may be deployed as a client computing device in a patient environment 102 and specifically configured with logic elements, data structures, and the like, to implement the patient interaction system 110 described previously above, including all resources necessary to facilitate the specific operations attributed to the patient interaction system 110 in the discussion above.

Moreover, one or more data processing systems such as depicted in FIG. 2 may be deployed in a distributed data processing system, communicatively coupled to one another via one or more data networks and corresponding data network devices, and to client computing devices deployed in patient environments. Such data processing system(s) may be specifically configured with logic elements, data structures, and the like, to implement the cognitive patient translation system 120 described previously above, including all resources necessary to facilitate the specific operations attributed to the patient interaction system 110 in the discussion above. In some embodiments, such resources, logic elements, and data structures may be distributed across multiple ones of these data processing systems, and in other illustrative embodiments, they may be implemented on a single data processing system operating as a server to the patient interaction system 110 which may be implemented on a client computing device.

In the depicted example of FIG. 2, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example flowchart outlining an operation for learning patient indicators and their associations with concepts in accordance with one illustrative embodiment. As shown in FIG. 3, the operation starts by initiating a learning session with the patient via the patient interaction system 110 (step 310). As part of the learning session, the patient interaction system 110 presents concept prompts/stimuli, which may be audible, visual, or the like, and monitors the patient's response to the prompts/stimuli using one or more monitoring devices (step 320). The input from the monitoring device(s) is analyzed to extract or identify one or more patient indicators (step 330). As mentioned previously, various applications or logic may be used to analyze the input from the monitoring devices, such as voice to text conversion, natural language processing, image analysis, writing analysis, etc. which may be implemented by the patient interaction system 110 to perform a processing of the input to extract the salient features that are indicative of a patient indicator.

The patient indicator(s) extracted or identified in the monitored input are then associated with the corresponding concept of the concept prompt/stimulus that caused the patient's response (step 340). This process is repeated for multiple different concepts, different prompts/stimuli (potentially of the same concept), and for multiple different sessions so as to build an understanding of how the particular patient communicates various concepts.

Having collected the patient indicator association information over multiple learning sessions, the cognitive patient translation system generates values indicating the strength of associations between patient indicators and concepts in an ontology (step 350). This may include utilizing a function to correlate frequency of occurrence of patient indicators, as well as other factors, with the concept to generate a relative scoring of the strength of the association of the patient indicator with the particular concept. This gives an indication that should the patient exhibit the patient indicator, the likelihood that the patient is meaning to communicate the corresponding concept. As discussed above, this operation may further include propagating strengths through a concept ontology to related concepts.

The resulting patient indicator ontology database, which is specifically tailored to the particular patient and their particular way of communicating concepts, is then provided to the cognitive patient translation system 120 for use in translating patient indicators for the patient in future interactions (step 360). The operation then terminates.

Figure 4:
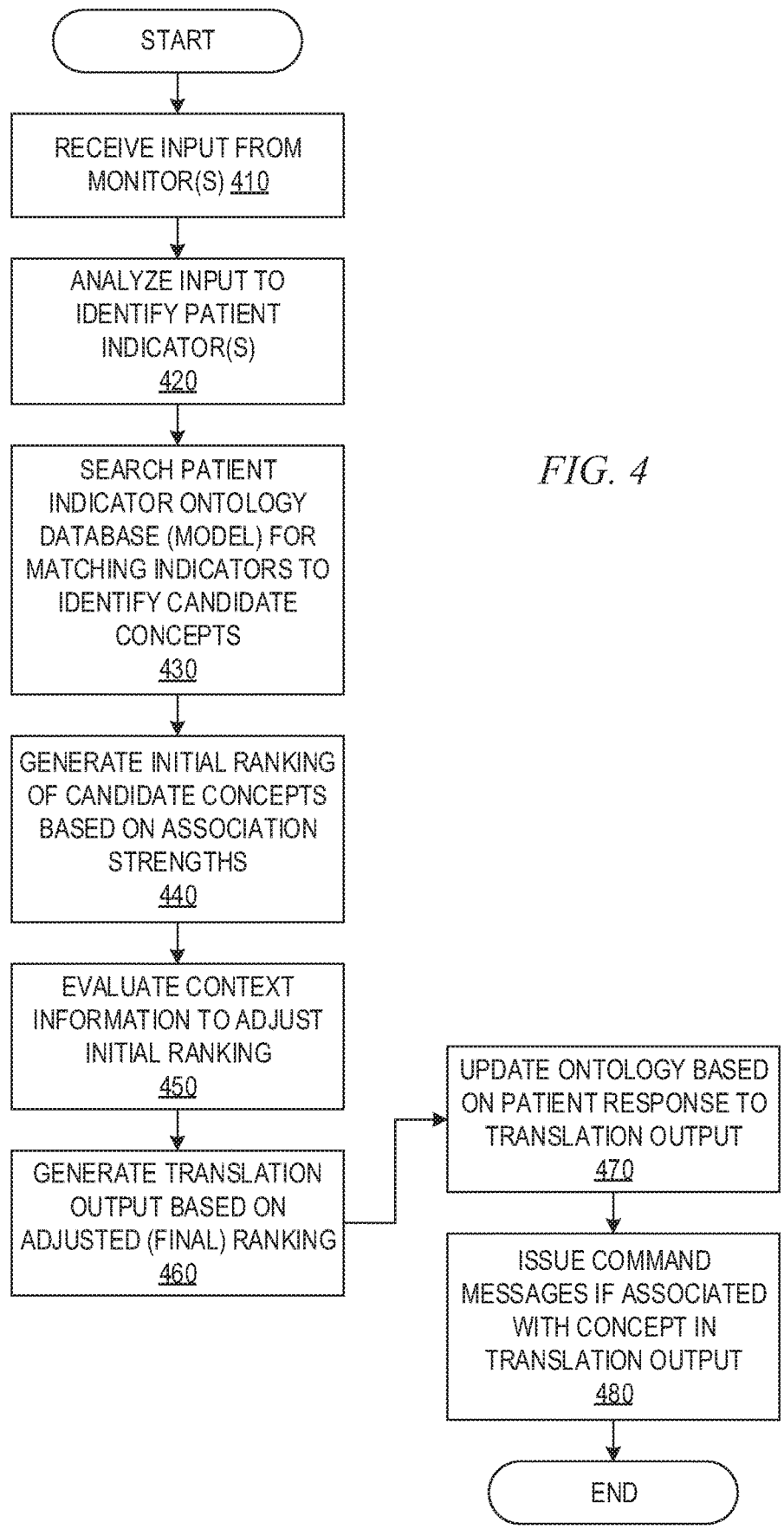
FIG. 4 is an example flowchart outlining an operation for translating patient indicators into concepts in accordance with one illustrative embodiment.

FIG. 4 is an example flowchart outlining an operation for translating patient indicators into concepts in accordance with one illustrative embodiment. As shown in FIG. 4, the operation starts by receiving one or more inputs from monitoring device(s) comprising a captured communication from the patient (step 410). The input received from the monitoring device(s) is analyzed to extract or identify any patient indicator(s) present in the input (step 420). This again may comprise various different types of algorithms similar to step 330 in FIG. 3 above.

The patient indicator(s) identified in the input are used as a basis to query or search the patient indicator ontology database associated with the patient for matching entries having the patient indicator(s) and thereby identify candidate concepts that the patient may be attempting to communicate (step 430). The candidate concepts have associated strengths of association between the patient indicator(s) and the candidate concepts that have been learned through the learning process previously described. These strengths may be used to generate an initial ranking of the candidate concepts relative to one another (step 440).

Context information for the inputs from the monitoring device(s) may be further evaluated to adjust the strengths or ranking scores associated with the candidate concepts and thereby modify the relative ranking of the candidate concepts (step 450). The cognitive patient translation system 120 then generates a translation output based on the final relative ranking of the candidate concepts (step 460). The patient may respond to this translation output by providing an indication as to whether it is correct or not and the patient indicator ontology database may be updated accordingly by modifying the strengths of association to increase/decrease the strengths based on whether or not the patient indicated the response to be correct or incorrect (step 470). Moreover, in cases where the translation output indicates a concept for which there is an automated command associated with it, a corresponding command message may be output to a device in the patient's environment to cause a corresponding action to occur, e.g., turn on/off the television, turn up/down the volume, etc. (step 480). The operation then terminates.

Thus, the illustrative embodiments provide mechanisms for assisting patients who have difficulty communicating concepts by providing a functionality for learning the particular way that a patient communicates the concepts. Moreover, the illustrative embodiments provide mechanisms for translating patient indicators, which may not be readily understandable to other persons not afflicted with cognitive issues, into expressions of concepts that are readily understandable to those persons so that they may attend to the needs of the patient and carry on conversations with the patient. Furthermore, in some illustrative embodiments, the mechanisms provide functionality for automatically controlling devices within a patient's environment based on a translation of the patient's indicators into corresponding concepts.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to specifically configure the at least one processor to implement a cognitive patient translation system, the method comprising:

performing a machine learning operation, by the cognitive patient translation system, to learn, for a particular patient, associations between patient indicators and concepts that the patient is attempting to communicate or concepts representing actions that the patient would like to perform within a patient environment;

receiving, by the cognitive patient translation system from a monitoring device in the patient environment, a patient input representing an attempt by the patient to communicate a concept or interact with the patient environment;

performing, by the cognitive patient translation system, a cognitive translation of one or more patient indicators in the patient input to one or more corresponding concepts based on results of the machine learning operation; and generating, by the cognitive patient translation system, a translation output specifying the one or more corresponding concepts.

2. The method of claim 1, wherein the machine learning operation is specifically configured for patients afflicted with a cognitive impairment or communication impairment.

3. The method of claim 2, wherein the cognitive impairment or communication impairment is Wernicke's aphasia.

4. The method of claim 1, wherein the patient indicators comprise at least one of an audible utterance from the patient, a motion or gesture performed by the patient, or a written input of a shape, contour, or word generated by the patient.

5. The method of claim 1, wherein performing the machine learning operation comprises:

monitoring, over a period of time, the particular patient's responses to concept prompts or concept stimuli;

analyzing the patient's responses to the concept prompts or concept stimuli to identify patient indicators present in the patient's responses;

associating instances of patient indicators in the patient's responses to concepts present in a computer model associated with the particular patient; and determining, for each concept in the computer model, and for each patient indicator associated with each concept in the computer model, a strength of association between the concept and the patient indicator.

6. The method of claim 5, wherein the strength of association between the concept and the patient indicator is determined based on a function of a number of instances of the patient indicator being identified in patient responses to concept prompts or concept stimuli associated with the concept as part of the monitoring.

7. The method of claim 6, wherein the function of the number of instances further comprises a weighted function, where the weights identify a relative number of instances of the patient indicator in the patient responses to the concept prompts or concept stimuli associated with the concept compared to numbers of instances of other patient indicators in patient responses to the concept prompts or concept stimuli associated with the concept.

8. The method of claim 6, wherein the function of the number of instances further comprises a weighted function that more heavily weights patient indicators that are more recently utilized by the patient in patient responses than other patient indicators that are used less recently in patient responses by the patient.

9. The method of claim 1, further comprising:

identifying, based on results of the cognitive translation, a corresponding concept representing an action the patient wants to perform with a device present in the patient environment;

automatically generating, by the cognitive translation system, a command to cause the device present within the patient environment to perform the action; and automatically transmitting, by the cognitive translation system, the command to the device to cause the device to perform the action.

10. The method of claim 1, wherein the cognitive translation system is distributed across a local computing device present within the patient environment, and a remotely located computing system in communication with the local computing device via one or more data networks, and wherein the local computing device receives the patient input and outputs the translation output, and wherein the remotely located computing system performs the machine learning operation and performs the cognitive translation.

11. A computer program product comprising a non-transitory computer readable medium having a computer readable program stored therein, wherein the computer readable program, when executed on a computing device, causes the computing device to implement a cognitive patient translation system which operates to:

perform a machine learning operation to learn, for a particular patient, associations between patient indicators and concepts that the patient is attempting to communicate or concepts representing actions that the patient would like to perform within a patient environment;

receive, from a monitoring device in the patient environment, a patient input representing an attempt by the patient to communicate a concept or interact with the patient environment;

perform a cognitive translation of one or more patient indicators in the patient input to one or more corresponding concepts based on results of the machine learning operation; and generate a translation output specifying the one or more corresponding concepts.

12. The computer program product of claim 11, wherein the machine learning operation is specifically configured for patients afflicted with a cognitive impairment or communication impairment.

13. The computer program product of claim 12, wherein the cognitive impairment or communication impairment is Wernicke's aphasia.

14. The computer program product of claim 11, wherein the patient indicators comprise at least one of an audible utterance from the patient, a motion or gesture performed by the patient, or a written input of a shape, contour, or word generated by the patient.

15. The computer program product of claim 11, wherein the computer readable program further causes the cognitive patient translation system to perform the machine learning operation at least by:
- monitoring, over a period of time, the particular patient's responses to concept prompts or concept stimuli;
- analyzing the patient's responses to the concept prompts or concept stimuli to identify patient indicators present in the patient's responses;
- associating instances of patient indicators in the patient's responses to concepts present in a computer model associated with the particular patient; and
- determining, for each concept in the computer model, and for each patient indicator associated with each concept in the computer model, a strength of association between the concept and the patient indicator.

16. The computer program product of claim 15, wherein the strength of association between the concept and the patient indicator is determined based on a function of a number of instances of the patient indicator being identified in patient responses to concept prompts or concept stimuli associated with the concept as part of the monitoring.

17. The computer program product of claim 16, wherein the function of the number of instances further comprises a weighted function, where the weights identify a relative number of instances of the patient indicator in the patient responses to the concept prompts or concept stimuli associated with the concept compared to numbers of instances of other patient indicators in patient responses to the concept prompts or concept stimuli associated with the concept.

18. The computer program product of claim 16, wherein the function of the number of instances further comprises a weighted function that more heavily weights patient indicators that are more recently utilized by the patient in patient responses than other patient indicators that are used less recently in patient responses by the patient.

19. The computer program product of claim 11, wherein the computer readable program further causes the cognitive patient translation system to:
- identify, based on results of the cognitive translation, a corresponding concept representing an action the patient wants to perform with a device present in the patient environment;
- automatically generate a command to cause the device present within the patient environment to perform the action; and
- automatically transmit the command to the device to cause the device to perform the action.

20. An apparatus comprising:
a processor; and
a memory coupled to the processor, wherein the memory comprises instructions which, when executed by the processor, cause the processor to implement a cognitive patient translation system which operates to:
perform a machine learning operation to learn, for a particular patient, associations between patient indicators and concepts that the patient is attempting to communicate or concepts representing actions that the patient would like to perform within a patient environment;
receive, from a monitoring device in the patient environment, a patient input representing an attempt by the patient to communicate a concept or interact with the patient environment;
perform a cognitive translation of one or more patient indicators in the patient input to one or more corresponding concepts based on results of the machine learning operation; and
generate a translation output specifying the one or more corresponding concepts.

* * * * *